United States Patent

Cross et al.

[11] Patent Number: 5,135,199
[45] Date of Patent: Aug. 4, 1992

[54] VALVES AND URINE BAGS

[75] Inventors: David E. Cross, Rustington; Peter J. Briggs; Kenneth J. Brooks, both of Lancing, all of England

[73] Assignee: Smiths Industries Public Limited Company, London, England

[21] Appl. No.: 783,254

[22] Filed: Oct. 28, 1991

[30] Foreign Application Priority Data

Nov. 7, 1990 [GB] United Kingdom ........... 9024244

[51] Int. Cl.$^5$ .............................. F16K 31/00
[52] U.S. Cl. ........................ 251/319; 251/347; 251/353; 251/904; 604/326
[58] Field of Search ........... 251/353, 347, 904, 319; 604/323, 326

[56] References Cited

U.S. PATENT DOCUMENTS

| | | | |
|---|---|---|---|
| 1,458,718 | 6/1923 | Lord | 251/353 |
| 2,841,314 | 7/1958 | Munson et al. | 251/353 |
| 4,280,498 | 7/1981 | Jensen | 604/323 |
| 4,423,741 | 1/1984 | Leny | 604/323 |
| 4,462,510 | 7/1984 | Steer et al. | 604/323 |
| 4,629,159 | 12/1986 | Wellenstam | 604/326 |
| 4,728,324 | 3/1988 | Steigerwald et al. | 604/323 |
| 4,909,478 | 3/1990 | Steer | 604/323 |
| 4,936,837 | 6/1990 | Wexler et al. | 604/326 |

FOREIGN PATENT DOCUMENTS 0389402 9/1990 European Pat. Off. .

Primary Examiner—A. Michael Chambers
Attorney, Agent, or Firm—Pollock, VandeSande and Priddy

[57] ABSTRACT

A valve for a urine collection bag has a base plate with a valve housing within which a valve member is displaceable. The valve member is hollow and has an aperture that aligns with an aperture in the base plate and bag when the valve member is in its lower position. The valve is opened by squeezing a finger plate on the valve member down towards a lower finger grip on the base plate. In the open position, the valve member can engage a coupling which slots between the arms of a fork projection on the base plate. The valve is closed by squeezing the finger plate up towards an upper finger grip on the base plate.

11 Claims, 2 Drawing Sheets

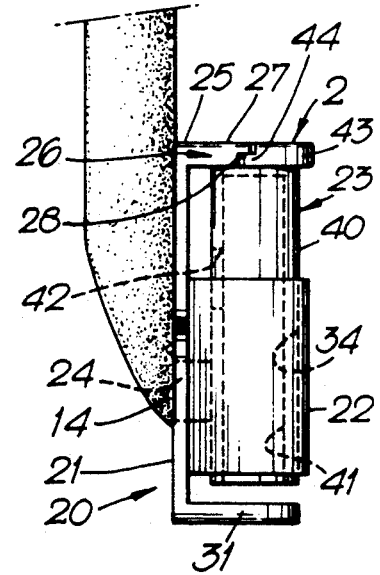
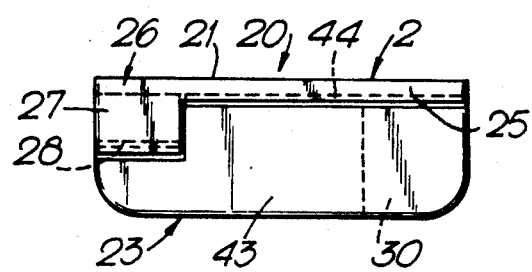
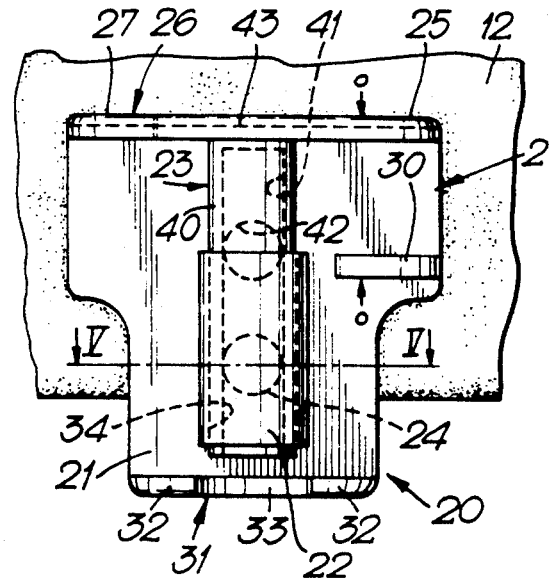
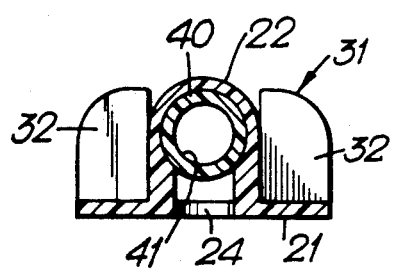
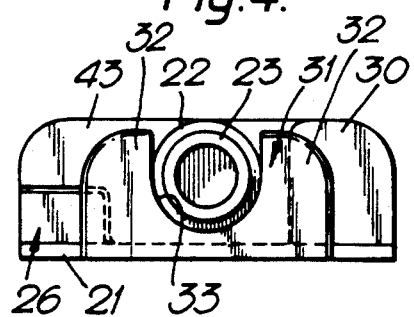

VALVES AND URINE BAGS

BACKGROUND OF THE INVENTION

This invention relates to valves and to urine bags including valves.

Urine collecting bags are used for collecting urine from a urostomy, a uretheral catheter or a penile sheath. The bag has an inlet at its upper end and an outlet at its lower end with a valve which is normally closed but which can be opened by the wearer to discharge urine when the bag becomes full.

Various different kinds of valves have been described previously, such as in GB 2101274, GB 2061466, GB 2129912 and GB 2166222.

The problem with previous valves is that they require some manual dexterity to operate. Because the wearers of urine bags tend to be elderly or infirm, they often lack the required dexterity, consequently, they experience difficulty in opening or closing the valve. The valves often require two hands to operate. Furthermore, it is not always obvious to the user whether the valve is open or closed, leading to the risk of leakage if the valve is inadvertently left open.

BRIEF SUMMARY OF THE INVENTION

It is an object of the present invention to provide an improved form of valve.

According to one aspect of the present invention there is provided a valve including a base member with a valve housing, an aperture opening into the valve housing, and a valve member located in the valve housing displaceable along the housing between a first position in which the valve member blocks flow of fluid out of the aperture and a second position in which the valve member allows flow of fluid out of the aperture, the valve member and base member both having finger grips so located that, when squeezed together in one way, the valve member is displaced to its first position and the valve is closed, and when squeezed together in another way the valve member is displaced to its second position and the valve is opened.

The base member preferably has two finger grips spaced from one another in a direction parallel to the length of the valve member such that squeezing the finger grip on the valve member towards one of the finger grips on the base member moves the valve member to the first position and squeezing the finger grip on the valve member towards the other of the finger grips on the base member moves the valve member to the second position. The finger grips on the base member may be located on opposite sides of the valve housing. The finger grip on the valve member is preferably a flat plate which is gripped on one side to move the valve member to the first position and on the other side to move the valve member to the second position. The valve member may be hollow along the lower part at its length and have an aperture opening into the valve housing when the valve member is in the second position such that fluid can flow through the valve member. The valve member may project from the lower end of the valve housing in the second position and the lower end of the valve member may be shaped to mate with a fluid connector. The base member may have a locating projection adapted to engage the connector. The locating projection is preferably adapted to prevent axial movement of the connector, lateral movement being prevented by engagement with the valve member. The locating projection is preferably of fork shape. The valve may include locking means adapted to prevent inadvertent opening of the valve.

According to another aspect of the present invention there is provided a valve including a valve housing and a valve member that is located in the housing and is displaceable along the housing between a first position in which the valve member blocks flow of fluid and a second position in which the valve member allows flow of fluid and in which the lower end of the valve member projects from the valve housing, the valve including locating means adapted to retain a cooperating connector and prevent movement of the connector axially of the valve member such that when the valve member is in its second position it engages the coupling in a fluid-tight connection and prevents lateral movement of the connector whereby the connector can only be disconnected when the valve member is displaced to its first position.

According to a further aspect of the present invention there is provided a urine bag including a valve according to the above one or other aspect of the present invention A urine bag including a valve, in accordance with the present invention, will now be described, by way of example, with reference to the accompanying drawings.

BRIEF DESCRIPTION OF THE DRAWINGS

FIG. 1 is a side elevation of the urine bag and valve;

FIG. 2 is a plan view of the valve from above;

FIG. 3 is a front elevation of the valve in the closed position;

FIG. 4 is a view of the underside of the valve;

FIG. 5 is a section along the line V—V of FIG. 3;

DETAILED DESCRIPTION OF THE PREFERRED EMBODIMENT

Figure 6:
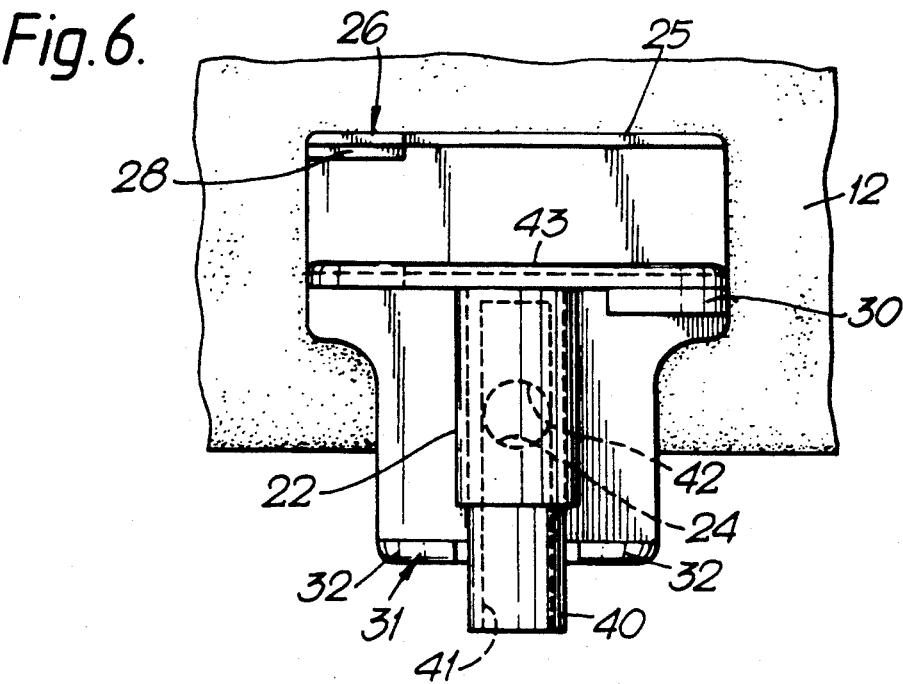
FIG. 6 is a front elevation of the valve in the open position.

With reference to FIG. 1, the urine bag 1 has two flexible walls 11 and 12 welded together around their periphery. One end of an inlet tube 13 is sealed to the bag 1 at its upper end, the other end of the inlet tube extending to a urinary sheath or urethral catheter (not shown). At its lower end, the front wall 12 of the bag has an outlet aperture 14 and a valve 2 which is normally closed but which can be opened to allow the contents of the bag to drain away.

The valve 2 will now be described in greater detail with reference to FIGS. 2 to 5. The valve 2 is a two-part assembly comprising a first integral moulding 20 of a rigid plastics material including a base-plate 21 and a valve housing 22, and a second moulding being a separate valve member 23 which is located in the housing. The base plate 21 is a flat T-shape plate the rear surface of which is welded to the front wall 12 of the bag 1. An aperture 24 extends through the base-plate 21 and is located midway across the base-plate about one third of the way from its lower end. The aperture 24 in the base-plate 21 overlies the outlet aperture 14 of the bag. Across the upper end of the base-plate 21 there is a forwardly projecting ledge 25. Along the major part of the width of the ledge 25 it has a narrow depth, projecting from the base-plate by a distance substantially equal to the thickness of the base-plate. At its left-hand end, as viewed in FIGS. 2 and 3, the ledge 25 is increased in depth to about three times that of the right-hand part of the ledge, forming a first finger grip 26 which extends along about one quarter of the length of the ledge. The finger grip 26 has a flat upper surface 27 and has an undercut lip 28 extending across its forward edge.

A second finger grip 30 projects perpendicularly from the forward surface of the baseplate 21 at a position about half way along its length and towards the right-hand edge of the base-plate. The second finger grip 30 is of rectangular shape and is larger than the first finger grip 26, projecting forwardly from the base-plate by about twice the distance of the first finger grip.

The base-plate 21 also has connector-supporting fork 31 which projects forwardly at the lower end of the base-plate. The fork 31 is of U-shape with two parallel arms 32 having rounded outer edges and separated by a semi-circular recess 33.

The valve housing 22 extends vertically on the forward surface of the base-plate 21, being located to overlie the aperture 24. The external surface of the housing 22 is U-shape in section and is about half the length of the baseplate 21 extending from a point level with the upper surface of the second finger grip 30 downwardly to a short distance above the fork 31. The housing 22 has a bore 34 extending through it, along its length, the bore being of circular section and the aperture 24 in the base-plate opening into the bore.

The second part of the valve 2, that is, the valve member 23, is also an integral, one-piece moulding of rigid plastics material. The valve member 23 has a vertical stem 40 of circular external section with the same diameter as the bore 34 through the housing 22. The stem 40 is located in the bore 34 as a close sliding fit which provides a fluid-tight seal with the bore. The length of the stem 40 is just less than that of the base-plate 21. The stem 40 is hollow, having a bore 41 that opens at its lower end and extends along the length of the stem, being closed at its upper end. A circular aperture 42 is located on the rear of the stem 40 towards its upper end and opens into the bore 41, the aperture in the stem being of the same size as the aperture 24 in the baseplate 21.

At its upper end, the valve member 23 has a flat, generally rectangular lateral plate 43 which extends across the width of the base-plate 21 and which has a depth equal to that of the second finger grip 30. The rear of the plate 43 is cut away at its left hand end over that portion aligned with the first finger grip 26. Along the rear edge of the plate 43 the top surface is cut away to about half the thickness of the plate to form a lip 44. In the position shown in FIGS. 1 to 5, the lip 44 on the plate 43 projects beneath the ledge 25 and the lip 28 on the base-plate 21 to limit upward displacement of the valve member. The plate 43 provides a third finger grip.

The valve is assembled by inserting the stem 40 of the valve member 23 into the top end of the bore 34 through the housing 22, and pushing the valve member down until the lower surface of the plate 43 contacts the top of the ledge 25 and finger grip 26. The valve member 23 is then pushed down further with increased pressure so that the base-plate 21 bends and snaps back when the plate 43 clears the ledge 25 and finger grip 26. The finger grips 26 and 30 on the base-plate 21 are spaced from one another in a direction parallel to the length of the valve member. When assembled, the finger grip 43 on the valve member is located intermediate the two finger grips 26 and 30 on the base-plate.

In the position shown in FIGS. 1 to 5, the valve member 23 is in its uppermost position, with the plate 43 in abutment with the underside of the ledge 25 and the finger grip 26. The aperture 42 in the valve stem 40 is displaced above the aperture 24 in the base-plate 21 which is occluded by the lower part of the valve stem so that flow out of the aperture is prevented. The valve is, therefore, closed.

Figure 7:
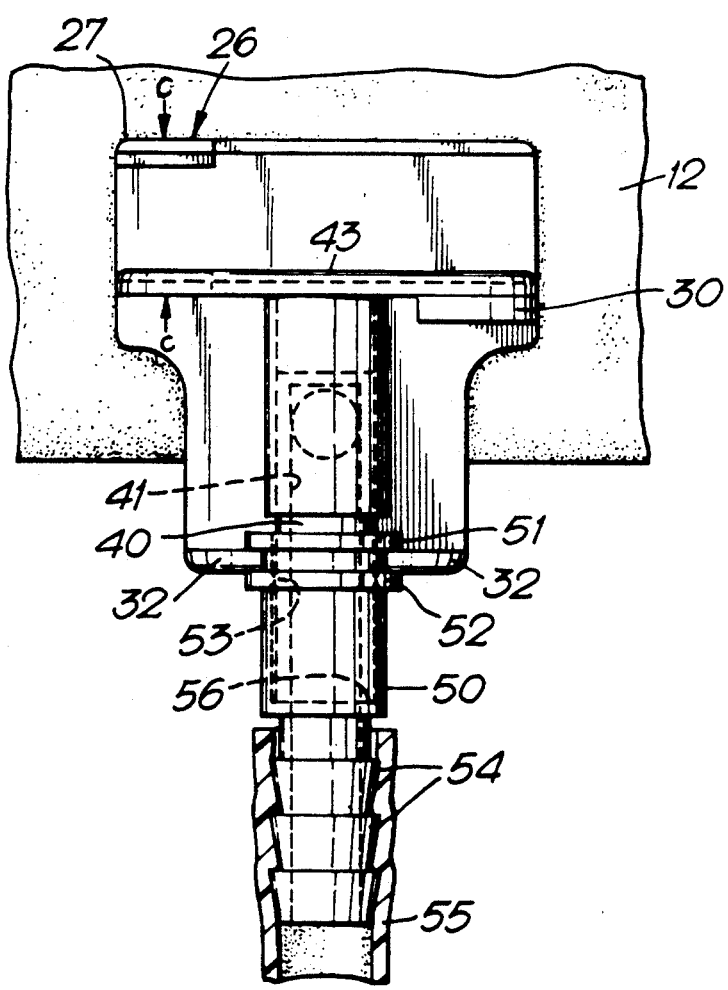
FIG. 7 is a front elevation of the valve in the open position coupled with a connector.

In order to open the valve, the user places a finger beneath the second finger grip 30 and his thumb on top of that part of the plate 43 above the second finger grip, and squeezes together as shown by the arrows "O" in FIG. 3. The plate 43, and hence the valve member 23, is thereby pushed down relative to the housing 22. The valve member 23 is pushed down to its full extent which is limited by engagement of the lower surface of the plate 43 with both the top of the valve housing 22 and the second finger grip 30. In this open position, the aperture 42 in the valve stem 40 is aligned with aperture 24 in the housing 22 of the base-plate 21, as shown in FIGS. 6 and 7. Urine in the bag 1 can then flow out of the aperture 24 into the valve housing 22 and through aperture 42 and into the bore 41 of the stem 40, exiting at its lower end. When the valve member 23 is pressed down to this position, the lower end of the valve stem 40 projects between and below the two arms 32 of the fork 31 on the base-plate 21 so that the fork does not provide any obstruction to the flow of urine out of the valve 2.

The valve 2 is closed again by squeezing the finger grips together in a different way. The user places his finger beneath the plate 43 on its left-hand side and places his thumb on the upper surface 27 of the first finger grip 26, at the top of the baseplate 21. By squeezing the plate 43 towards the first finger grip, as shown by the arrows "C" in FIG. 7, the valve member 23 is raised to the position shown in FIGS. 1 and 3.

The valve 2 can, therefore, be easily operated by one hand. Because the opening and closing movements are in a direction along the valve member through which the urine is discharged, there is a reduced risk of the flow of urine being misdirected, compared with previous valves involving a lateral opening/closing movement. The downward, opening movement of the valve is readily associated by the user with the downward flow of discharged urine so the user can readily ascertain the state of the valve. The valve lacks the rotatable levers of some previous valves which makes it less prone to inadvertent actuation by catching on the user's clothing. This is an important advantage because the bag is usually worn beneath clothing.

It is common practice with urine bags to leave the valve open at night and connect the outlet to a separate bag or drainage bottle. This is because the limited capacity of the bag may be excreded by urine discharge during the time that the wearer is asleep. The valve of the present invention is readily connected to such a drainage bottle (not shown) by means of a night connector 50 shown in FIG. 7.

The night connector 50 is moulded of a semi-rigid plastics material and is of generally tubular shape and circular section. Around its upper end, the connector has two external annular collars 51 and 52 which are spaced from one another along the connector by a distance slightly greater than the thickness of the fork 31 on the base-plate 21. The internal diameter of the connector 50 at its upper end is the same as the external diameter of the valve stem 40, the connector having a shallow internal bead 53 a short distance below the opening which makes a fluid-tight sliding seal with the stem. At its lower end, the connector has a reduced diameter and is formed with external barbs 54 which securely retain the end of the drainage tubing 55 to which the connector is coupled. Internally, the connector 50 has an annular step 56 just above the barbed lower end where the bore through the connector reduces in diameter. The connector 50 is assembled on the valve 2 in its closed position by pushing it into the space between the two arms 32 of the fork 31 so that the collars 51 and 52 lie above and below the fork respectively. The semi-circular recess 33 in the fork 31 is of the same diameter as the connector 50 so that it is located snugly in position. The valve member 23 is then pushed down so that the lower end of the valve stem 40 enters the top of the connector 50 and locks it firmly in position. When pushed fully down, the lower end of the valve stem 40 abuts the step 56 within the connector, the internal diameter of the stem 40 being the same as the diameter of the lower part of the connector so that there is an uninterrupted path for the flow of urine into the drainage tube 55. The connector 50 cannot be removed until the valve 2 is closed because the fork 31 prevents axial movement of the connector whereas lateral movement is prevented by engagement with the valve member 23 thereby providing positive security against inadvertent disconnection. The connector 50 can be rotated relative to the valve 2 when coupled to the valve, to enable the drainage tubing 55 to be directed as required, without kinking.

When used with a night connector, it is important that the valve is not inadvertently closed since this could result in overfilling of the bag. Because the present construction avoids the rotatable levers present in some previous valves, there is less risk of the valve catching on bed clothing and being inadvertently closed.

The valve could take many different forms. For example, the stem of the valve member could be solid with the valve housing being extended to form a spout through which urine is discharged. The shape and disposition of the finger grips could also be different from that described.

The valve could have a lock or detent to prevent inadvertent opening. In one form, this might comprise a vertical arm projecting from the plate 43 between the second finger grip 30 and the valve housing 22. A tooth projecting from the right-hand surface of the arm would engage the upper surface of the finger grip 30 when the valve member 23 was in its open position, so as to prevent downward displacement of the valve member. In order to open the valve, the user would have to push the arm over to the left so that the tooth clears the finger grip thereby enabling the valve member to be depressed. When raised to its closed position, the tooth would snap back in place above the finger grip 30.

The urine bag need not have a tubular inlet of the kind described since the bag could be a urostomy bag where the urine inlet is an opening in the rear wall of the bag which is sealed to the skin of the wearer about a surgically made stoma through which urine is discharged. Although the valve has been described on a urine bag it could also be used in other applications.

What we claim is:

1. A valve comprising: a base member, a valve housing on the base member, an aperture in the base member opening into the valve housing, and an elongated valve member located in the valve housing and displaceable along its length in the housing between a first position in which the valve member blocks flow of fluid out of the aperture and a second position in which the valve member allows flow of fluid out of the aperture, the base member having two finger grips spaced from one another in a direction parallel to the length of the valve member, the valve member having a plate located intermediate the two finger grips on the base member such that the valve member can be displaced along its length to the first position by squeezing one side of the plate on the valve member toward one finger grip on the base member and such that the valve member can be displaced along its length in an opposition direction to the second position by squeezing the other side of the plate on the valve member toward the other finger grip on the base member.

2. A valve comprising: a base member having a valve housing, and an elongated valve member located in the housing and displaceable along its length in the housing between a first position in which the valve member blocks flow of fluid and a second position in which the valve member allows flow of fluid and in which a lower end of the valve member projects from the valve housing, said base member including locating means shaped to retain a cooperating connector and to prevent movement of the connector axially of the valve member, and the projecting lower end of the valve member in its second position being adapted to engage the connector in a fluid-tight connection and to prevent lateral movement of the connector whereby the connector can be disconnected only when the valve member is in its first position.

3. In a valve of the kind including a base member with a valve housing, an aperture opening into the valve housing and a valve member located in the valve housing that is displaceable in the housing between a first position in which the valve member blocks flow of fluid out of the aperture and a second position in which the valve member allows flow of fluid out of the aperture, the improvement wherein the valve member is elongated in configuration and slidable along its length relative to a base member, the valve member and base member both having a pair of finger grips so located that when a first finger grip on the valve member and a first finger grip on the base member are squeezed together the valve member is slidably displaced along the housing to its first position and the valve is closed, and when a second finger grip on the valve member and a second finger grip on the base member are squeezed together the valve member is slidably displaced along the housing to its second position and the valve is opened.

4. A valve according to claim 3, wherein the pair of finger grips on the base member are located respectively on opposite sides of the valve housing.

5. A valve according to claim 1 wherein one of the pair of finger grips on the valve member is provided by one side of a flat plate, and the other of said pair of finger grips on the valve member is provided by an opposite side of said flat plate.

6. A valve according to claim 3, wherein the valve member is hollow along a lower part at least of its length and has an aperture that aligns with the aperture opening into the valve housing when the valve member is in the second position such that fluid can flow through the valve member.

7. A valve according to claim 6, wherein the valve member projects from a lower end of the valve housing in the second position.

8. A valve according to claim 7, wherein a lower end of the valve member is shaped to mate with a fluid connector.

9. A valve according to claim 8, wherein the base member has a locating projection shaped to engage the fluid connector.

10. A valve according to claim 9 wherein the locating projection is adapted to prevent axial movement of the connector, and wherein the valve member prevents lateral movement of the connector when it mates with the connector.

11. A valve according to claim 9, wherein the locating projection is of fork shape.

* * * * *